United States Patent
Al-Furaih

(10) Patent No.: US 11,123,384 B2
(45) Date of Patent: *Sep. 21, 2021

(54) MICROENCAPSULATED PROBIOTIC BACTERIA

(71) Applicant: Imam Abdulrahman Bin Faisal University, Dammam (SA)

(72) Inventor: Lulwah Yousef Abdullateef Al-Furaih, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/005,425

(22) Filed: Jun. 11, 2018

(65) Prior Publication Data

US 2018/0289755 A1 Oct. 11, 2018

Related U.S. Application Data

(63) Continuation of application No. 15/013,261, filed on Feb. 2, 2016, now Pat. No. 9,999,640.

(51) Int. Cl.
  *A61K 35/747* (2015.01)
  *A23L 33/135* (2016.01)
  *C12N 1/20* (2006.01)

(52) U.S. Cl.
  CPC .......... *A61K 35/747* (2013.01); *A23L 33/135* (2016.08); *C12N 1/20* (2013.01); *A23V 2002/00* (2013.01); *Y02A 50/30* (2018.01)

(58) Field of Classification Search
  CPC ....... A61K 35/747; C12N 1/20; A23L 33/135; A23V 2002/00; A23V 2200/224; A23V 2200/3204; A23V 2250/5026; Y02A 50/30; A23Y 2220/67
  See application file for complete search history.

(56) References Cited

U.S. PATENT DOCUMENTS

| 2010/0028449 A1 | 2/2010 | Prakash et al. |
| 2012/0058095 A1* | 3/2012 | Strozzi .................. A23D 9/007 424/93.44 |
| 2012/0263826 A1 | 10/2012 | Fang et al. |
| 2012/0308650 A1 | 12/2012 | Vegas et al. |
| 2014/0023693 A1 | 1/2014 | Guenzburg et al. |

FOREIGN PATENT DOCUMENTS

| WO | WO 2011/004375 A1 | 1/2011 |
| WO | WO 2015/000972 A1 | 1/2015 |

OTHER PUBLICATIONS

Gbasii et al., International Journal of Food Microbiology, 2009, vol. 129, p. 103-105.*
Adelfo García-Ceja, et al., "Viability during refrigerated storage in selected food products and during simulated gastrointestinal conditions of individual and combined lactobacilli encapsulated in alginate or alginate-chitosan", LWT—Food Science and Technology, vol. 63, Issue 1, Sep. 2015, pp. 482-489 (Abstract only).
W. Krasaekoopt, et al., "Effect of addition of inulin and galactooligosaccharide on the survival of microencapsulated probiotics in alginate beads coated with chitosan in simulated digestive system, yogurt and fruit juice", LWT—Food Science and Technology. vol. 57, Issue 2, Jul. 2014, pp. 761-766 (Abstract only).

* cited by examiner

*Primary Examiner* — Kade Ariani
(74) *Attorney, Agent, or Firm* — Oblon, McClelland, Maier & Neustadt, L.L.P.

(57) ABSTRACT

Microencapsulated probiotic bacteria protected from degradation by acidic aqueous solutions, high bile salt concentrations, elevated temperatures, and prolonged storage and having an increased anti-bacterial activity as compared to their non-microencapsulated counterparts. The microencapsulated probiotic bacteria comprise probiotic bacteria encapsulated in microcapsules. The probiotic bacteria comprise live *Lactobacillus plantarum* cells. Each of the microcapsules comprises a matrix of a gelled alginate. The matrix wholly envelops the probiotic bacteria within the matrix. An outer surface of the matrix has a coating consisting essentially of one vegetable oil selected from the group consisting of olive oil and canola oil, or an outer surface of the matrix is treated with sodium chloride. The microencapsulated probiotic bacteria have an average particle size of less than 1000 microns (μm) in diameter.

4 Claims, No Drawings

MICROENCAPSULATED PROBIOTIC BACTERIA

CROSS-REFERENCE TO RELATED APPLICATIONS

This application is a continuation of and claims the benefit of priority to U.S. application Ser. No. 15/013,261, now allowed, filed Feb. 2, 2016, the entire contents of which are incorporated herein by reference.

BACKGROUND OF THE INVENTION

Technical Field

The present disclosure relates to the field of microencapsulated probiotic bacteria and food or beverage products containing the microencapsulated probiotic bacteria. The microencapsulated probiotic bacteria are encapsulated in microcapsules, each of which comprises a matrix of a gelled alginate. An outer surface of the gelled alginate matrix is coated with a vegetable oil or treated with sodium chloride.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, is neither expressly nor impliedly admitted as prior art against the present invention.

Probiotic bacteria are live bacterial microbes that beneficially influence the health and nutrition of individuals by promoting a healthier microflora in the host's intestine and inhibiting pathogenic bacteria. Potential mechanisms of the anti-pathogenic effects of probiotic bacteria are through decreasing the luminal pH by the production of short chain fatty acids such as acetic acid, lactic acid or propionic acid, rendering vital nutrients unavailable to pathogens, altering the redox potential of the environment, producing hydrogen peroxide or producing bacteriocins or other inhibitory substances. Probiotic microflora are dependent on substances obtained from the diet of the host organism. Probiotic bacteria typically colonize in the large intestine and can serve either or both of at least two major roles: they can supplement the natural flora of the gastrointestinal tract with additional bacteria, and they can be effective in treating a number of health conditions, including, but not limited to (1) gastrointestinal tract related disorders (e.g., constipation and diarrhea caused by an infection by pathogenic organisms, antibiotics, chemotherapy, etc.); (2) stimulation and modulation of the immune system; (3) anti-tumoral effects resulting from inactivation or inhibition of carcinogenic compounds present in the gastrointestinal tract by reduction of intestinal bacterial enzymatic activities (e.g., 0-glucuronidase, azoreductase, nitroreductase, etc.); (4) reduced production of toxic final products (e.g., ammonia, phenols, other protein metabolites known to influence hepatic cirrhosis, etc.); (5) reduction of serum cholesterol and arterial pressure; (6) maintenance of mucosal integrity; (7) alleviation of lactose intolerance symptoms; and/or (8) prevention of vaginitis. Some of the most common types of probiotic bacteria include *Lactobacillus* and Bifidobacteria.

Probiotic bacteria are sensitive to various environmental conditions such as pH (many desirable probiotics grow best at pH values around 7.0), moisture, elevated temperatures, high concentrations of bile salts (e.g. 0.3% or higher for certain strains of probiotic bacteria), air and light, particularly UV light. When these conditions are not properly controlled, the viability (often measured in colony forming units (CFU), or as metabolic activity rates), and therefore the efficacy of probiotic bacteria can be substantially reduced.

To be used as beneficial and/or therapeutic agents in a diet, probiotic bacteria need to be protected (a) during the manufacturing process, e.g. when probiotic bacteria are supplemented to a food product that is baked or pasteurized at an elevated temperature; (b) during storage, either alone or in a carrier product, e.g. a food, such as fermented milk, e.g. yogurt, soft, semi-hard and hard cheese, ice cream, and frozen fermented dairy desserts; and (c) while passing through the digestive tract, especially the stomach with an acidic pH of about 2 and the intestines with bile salts. In dairy products such as yogurt, probiotic bacteria have to survive mildly acidic conditions (e.g. at a pH of about 4) for an extended period of time. Probiotic bacterial survival in products is affected by a range of factors, including pH, post-acidification (during storage) in fermented products, and storage temperatures. All these stresses result in death of a significant percentage of probiotic bacterial cells. Therefore, the typical standard for food sold with health claims related to probiotic bacteria is the inclusion of at least $10^9$-$10^{10}$ colony forming units (CFU) of viable probiotic bacteria per serving. The International Dairy Federation (IDF) suggests that a minimum of $10^7$ probiotic bacteria cells should be alive at the time of consumption per gram of the product, in order to achieve the claimed health benefits.

Encapsulation has been used to prevent damage to or degradation of probiotic bacteria during storage, exposure to elevated temperatures, and exposure to acidic and high bile salt environments, for example, when they pass through the gastrointestinal tract, and to increase the stability or viability of the probiotic bacteria. Encapsulation is a process of creating a matrix wholly enveloping a core of encapsulated material, i.e. probiotic bacteria. As a result, the matrix, with its outer surface facing the surrounding environment, provides the encapsulated probiotic bacteria a barrier to the surrounding environment. The matrix usually comprises one or more biopolymers. The matrix may be subsequently degraded to release the probiotic bacteria at a target site, e.g. the small intestine and/or colon. The microcapsules may range from submicron to several microns or larger up to 1000 microns in size, and can be of different shapes.

Several biopolymers, such as alginate, starch, xanthan gum, guar gum, locust bean gum, and carrageenan gum, may be used as matrix materials to protect probiotic bacteria. Refined from brown seaweeds, alginates are natural anionic polysaccharides made up by D-mannuronic and L-guluronic acid residues joined linearly by 1-4 glycosidic linkages. Alginates from different species of brown seaweed often have variations in their chemical structure, resulting in different physical properties. For example, some may yield an alginate that gives a strong gel, while others may yield a weaker gel. Alginates are commonly available as a sodium or potassium salt (i.e., sodium alginate or potassium alginate). Natural alginates may be chemically modified to obtain synthetic alginates with improved biocompatibility and more desirable physiochemical properties, such as alginate polymer stability, pore size, and hydrophobicity/hydrophilicity.

The viscosity of an alginate solution can vary, depending on the alginate concentration, length of the alginate molecules, or the number of monomer units in the chains, or the weight average molecular weight of an alginate polymer (the weight average molecular weight of sodium alginate typically ranges from 10,000 to 600,000 Da), with longer chains resulting in higher viscosities at similar concentrations. For example, a low viscosity sodium alginate available from Sigma Aldrich has a viscosity of 4-12 cP when dissolved in water at a concentration of 1% at 25° C. A medium viscosity sodium alginate available from Sigma Aldrich has a viscosity of no less than 2,000 cP when dissolved in water at a concentration of 2% at 25° C. A high viscosity sodium alginate available from Sigma Aldrich has a viscosity of about 14,000 cP when dissolved in water at a concentration of 2% at 25° C. When alginate is exposed to divalent cations, such as $Ca^{2+}$, $Mg^{2+}$, or $Fe^{2+}$, the alginate undergoes gelation. Alginate encapsulation is used due to its simple preparation, low cost, and good biocompatibility, since alginate does not affect the viability of most types of encapsulated probiotic bacteria. Although alginate encapsulation has shown a protective effect on the viability of different probiotic bacteria subjected to different stress factors, including low pH, bile salts, and storage (when incorporated in foods), the protective effect is mostly partial and inadequate.

Olive oil is a fat obtained from the olive (the fruit of *Olea europaea*; family Oleaceae), a traditional tree crop of the Mediterranean Basin. The oil is produced by pressing whole olives and is commonly used in cooking, cosmetics, pharmaceuticals, and soaps. Olive oil is composed mainly of the mixed triglyceride esters of oleic acid and palmitic acid and of other fatty acids, along with traces of squalene (up to 0.7%) and sterols (about 0.2% phytosterol and tocosterols).

Canola oil is a widely consumed vegetable oil and key ingredient in many foods. Its reputation as a healthy oil has created high demand in markets around the world. It typically contains about 61% oleic acid, about 21% linoleic acid, about 9-11% alpha-linolenic acid, about 7% saturated fatty acids, about 4% plamitic acid, about 2% stearic acid, and about 0.4% trans fat.

It is an object of this disclosure to provide compositions of microencapsulated probiotic bacteria that are protected from degradation by an acidic aqueous solution, an aqueous solution with a high concentration of bile salts, elevated temperatures, and/or prolonged storage, such that the microencapsulated probiotic bacteria are more viable and/or metabolically active than their non-microencapsulate counterparts.

BRIEF SUMMARY OF THE INVENTION

According to a first aspect, the present disclosure relates to microencapsulated probiotic bacteria comprising probiotic bacteria encapsulated in microcapsules. The probiotic bacteria comprise live *Lactobacillus plantarum* cells. Each of the microcapsules comprises a matrix of a gelled alginate. The matrix wholly envelops the probiotic bacteria within the matrix. An outer surface of the matrix has a coating consisting essentially of one vegetable oil. The vegetable oil is preferably selected from the group consisting of olive oil and canola oil. Alternatively, an outer surface of the matrix is treated with sodium chloride. The microencapsulated probiotic bacteria have an average particle size of less than 1000 microns (μm) in diameter.

In one or more embodiments, the thickness of the matrix of the gelled alginate is at least 250 μm.

In one or more embodiments, the matrix of the gelled alginate comprises an unmodified alginate, a modified alginate, or a combination thereof.

In one or more embodiments, the microcapsules protect the probiotic bacteria from being degraded by an acidic aqueous solution. In some embodiments, the microcapsules protect the probiotic bacteria from being degraded by the acidic aqueous solution having a pH of about 1-4. In other embodiments, the microencapsulated probiotic bacteria are more viable and/or metabolically active after a treatment with the acidic aqueous solution than the probiotic bacteria not encapsulated in microcapsules but otherwise treated with the acidic aqueous solution. In still other embodiments, the outer surface of the matrix has the coating consisting essentially of the olive oil, and at least 80% of the microencapsulated probiotic bacteria survive a treatment with the acidic aqueous solution having a pH of about 1-3 for at least about 1.5 hours.

In one or more embodiments, the microcapsules protect the probiotic bacteria from being degraded by an aqueous solution comprising bile salts at a concentration of about 0.1-1% of the total weight of the aqueous solution. In some embodiments, the microencapsulated probiotic bacteria are more viable and/or metabolically active after a treatment with the aqueous solution comprising the bile salts at a concentration of about 0.1-1% of the total weight of the aqueous solution than the probiotic bacteria not encapsulated in microcapsules but otherwise treated with the aqueous solution comprising the bile salts at a concentration of about 0.1-1% of the total weight of the aqueous solution. In other embodiments, the outer surface of the matrix is treated with the sodium chloride, and at least 98% of the microencapsulated probiotic bacteria survive a treatment with the aqueous solution comprising the bile salts at a concentration of about 0.2-0.5% of the total weight of the aqueous solution for at least about 2 hours. In still other embodiments, the outer surface of the matrix has the coating consisting essentially of the olive oil, and at least 80% of the microencapsulated probiotic bacteria survive a treatment with the aqueous solution comprising the bile salts at a concentration of about 0.4-0.7% of the total weight of the aqueous solution for at least about 2 hours.

In one or more embodiments, the microcapsules protect the probiotic bacteria from being degraded at a temperature of at least 65° C. for at least about 15 minutes. In some embodiments, the microencapsulated probiotic bacteria are more viable and/or metabolically active after being exposed to a temperature of at least 65° C. for at least about 15 minutes than the probiotic bacteria not encapsulated in microcapsules but otherwise exposed to the temperature of at least 65° C. for the at least about 15 minutes. In other embodiments, the outer surface of the matrix is treated with the sodium chloride, and at least 80% of the microencapsulated probiotic bacteria survive at a temperature of at least 65° C. for at least about 30 minutes.

In one or more embodiments, the microencapsulated probiotic bacteria are formulated as a supplement for a food or beverage product. In some embodiments, the food or beverage product is selected from the group consisting of yogurt, ice cream, cheese, chocolate, nutritional bars, cereal, milk, infant formulation, vegetable juices, and fruit juices.

According to a second aspect, the present disclosure relates to microencapsulated probiotic bacteria comprising probiotic bacteria encapsulated in microcapsules. The probiotic bacteria comprise live *Lactobacillus plantarum* cells. Each of the microcapsules comprises a matrix of a gelled alginate. The matrix wholly envelops the probiotic bacteria within the matrix. An outer surface of the matrix has a coating consisting essentially of olive oil. The microencapsulated probiotic bacteria have an average particle size of less than 1000 microns (μm) in diameter. The microcapsules protect the probiotic bacteria from being degraded at a temperature of about −30-10° C. for at least 7 days.

According to a third aspect, the present disclosure relates to microencapsulated probiotic bacteria comprising probiotic bacteria encapsulated in microcapsules. The probiotic bacteria comprise live *Lactobacillus plantarum* cells. Each of the microcapsules comprises a matrix of a gelled alginate. The matrix wholly envelops the probiotic bacteria within the matrix. An outer surface of the matrix has a coating consisting essentially of one selected from the group consisting of olive oil, canola oil, and chitosan, or an outer surface of the matrix is treated with sodium chloride. The microencapsulated probiotic bacteria have an average particle size of less than 1000 microns (μm) in diameter, and the microencapsulated probiotic bacteria display an increased anti-bacterial activity as compared to the probiotic bacteria not encapsulated in microcapsules. In some embodiments, the microencapsulated probiotic bacteria display the increased anti-bacterial activity against at least one selected from a group consisting of *E. coli, P. aeruginosa, E. aerogenes*, and *S. pyogenes*.

The foregoing paragraphs have been provided by way of general introduction, and are not intended to limit the scope of the following claims. The described embodiments, together with further advantages, will be best understood by reference to the following detailed description.

DETAILED DESCRIPTION OF THE EMBODIMENTS

Disclosed herein are compositions of microencapsulated probiotic bacteria.

A first aspect of the disclosure relates to microencapsulated probiotic bacteria comprising probiotic bacteria encapsulated in microcapsules. The probiotic bacteria comprise live *Lactobacillus plantarum* cells. Each of the microcapsules comprises a matrix of a gelled alginate. The matrix wholly envelops the probiotic bacteria within the matrix. An outer surface of the matrix has a coating consisting essentially of at least one vegetable oil. The vegetable oil is preferably selected from the group consisting of olive oil and canola oil. Alternatively, an outer surface of the matrix is treated with sodium chloride. The microencapsulated probiotic bacteria have an average particle size of less than 1000 microns (μm) in diameter.

In this disclosed microencapsulated probiotic bacteria composition, the matrix of the gelled alginate wholly envelopes the probiotic bacteria which form the core of the encapsulated material. As a result, the matrix, with its outer surface facing the surrounding environment, provides the encapsulated probiotic bacteria a barrier to the surrounding environment.

In one embodiment, the microencapsulated probiotic bacteria include only live *Lactobacillus plantarum* cells. In another embodiment, the microencapsulated probiotic bacteria include one or more other types of live probiotic bacterial besides *Lactobacillus plantarum*, non-limiting examples of which include the probiotic bacterial strains of *Bifidobacterium*, such as *B. breve, B. animalis (lactis), B. longum, B. bifidum, B. adolescentis, B. thermophilum*, and *B. infantis*, and other probiotic bacterial strains of the genus *Lactobacillus*, such as *L. acidophilus, L. casei, L. rhamnosus, L. paracasei, L. johnsonii, L. reuteri, L. lactis*, and *L. bulgaricus*. The ratio of one bacterial type, strain or species to the other(s) may vary widely. The ratio may be from about 0.00000001 to 1, about 0.0000001 to 1, about 0.000001 to 1, about 0.00001 to 1, about 0.0001 to 1, about 0.001 to 1, about 0.01 to 1, about 0.1 to 1, or about 1 to 1.

In some embodiments, the method of preparing the microencapsulated probiotic bacteria comprises mixing a sterile aqueous solution of an alginate salt, e.g. sodium alginate, at a concentration of 0.2-10% (w/w), preferably 0.5-8% (w/w), preferably 1-6% (w/w), preferably 1-4% (w/w), or preferably 2-3%, with the probiotic bacteria, which preferably are in the exponential growth phase as indicated, for example, by an $OD_{600-620}$ (nm) reading of 1, to form a first mixture. It is, however, also possible to encapsulate the probiotic bacteria that are in any other growth phase. The first mixture is combined with a gelation solution which can be an aqueous solution comprising one or more divalent cations, e.g. a calcium chloride solution at a concentration of 0.1-1 M or any suitable concentration, to initiate gelation of the alginate salt to form a second mixture. The second mixture is then passed through an opening, resulting in the formation of microcapsules having approximately the same diameter as the diameter of the opening. For instance, if the opening has a diameter of less than 1000 μm, microcapsules formed can have an average particle size of between 1 μm and 1000 μm in diameter. Extrusion can be optionally employed during formation of the microcapsules, in which the opening that the second mixture is passed through comprises a nozzle, for example, of an encapsulator, such as an Inotech Encapsulator™ IER-20 (Inotech Biosystems Intl. Inc. Switzerland), or the opening of a needle of an appropriate size attached to a syringe. In extrusion methods, the second mixture is forced through an extrusion nozzle or needle opening using pressure during the gelation process. It is within the skill of the art to select a suitable extrusion apparatus. The resulting microcapsules comprise the matrices of the gelled alginate that wholly envelops the probiotic bacteria within the matrices. In other embodiments, the method further comprises hardening the microcapsules in a calcium chloride solution for at least one, five, fifteen, thirty, or sixty minutes, followed by washing the hardened microcapsules with water. The optimal hardening time may vary, depending on the concentration and viscosity grade of the alginate salt, the type and concentration of the divalent cations in the hardening solution, the hardness of the microcapsules desired, the temperature of the hardening process and other parameters. In still other embodiments, the microcapsules are not subjected to hardening, but are washed with distilled sterile water.

Next, the outer surfaces of the gelled alginate matrices of the microcapsules are to be coated with at least one vegetable oil or treated with sodium chloride. Non-limiting examples of the vegetable oils suitable for the coating include soybean oil, sunflower oil, safflower oil, peanut oil, cottonseed oil, coconut oil, palm oil, rice bran oil, rapeseed oil, sesame oil, and preferably olive oil and canola oil, and their respective chemically modified oils, e.g. hydrogenated oils. For the coating of the outer surfaces of the gelled alginate matrices of the microcapsules with olive oil and/or canola oil, the washed microcapsules may be immersed in olive oil and/or canola oil for an effective period of time, e.g. 1 minute, 5 minutes, 10 minutes, or 30 minutes, or the olive oil and/or the canola oil can be sprayed on the outer surfaces of the gelled alginate matrices of the microcapsules to obtain a predetermined weight gain, e.g. a weight gain of about 10-50%, or about 15-45%, or about 20-40%, or about 30%, or to obtain a predetermined surface coverage with the oil, e.g. a coverage of at least 30%, at least 50%, at least 70%, or at least 90%.

In some embodiments, the outer surface of the gelled alginate matrix is coated with either olive oil or canola oil. In other embodiments, the outer surface of the gelled alginate matrix is coated with both olive oil and canola oil, with the ratio of the olive oil to the canola oil ranging from 20:1 to 1:20, from 15:1 to 1:15, from 10:1 to 1:10, from 5:1 to 1:5, or from 2:1 to 1:2. The olive oil and the canola oil may be of any type, grade, and origin, with a purity of at least 90%, preferably at least 95%, or more preferably at least 98%. Although the coating of the gelled alginate matrix preferably consists of olive oil and/or canola oil, the oils may contain certain impurities, including minerals (e.g. sodium, potassium, calcium, magnesium, and iron), proteins, and/or vitamins (e.g. vitamins A, C, and/or B6), at trace amounts, e.g. less than 10% (w/w), preferably less than 5% (w/w), preferably less than 2%, or more preferably less than 1% (w/w), without materially affecting the characteristics of the coated gelled alginate matrices of the microcapsules, including protection of the microencapsulated probiotic bacteria against an acidic aqueous environment, an aqueous environment with a high bile salt concentration, and an elevated temperature described below.

For the treatment of the outer surfaces of the gelled alginate matrices of the microcapsules with sodium chloride, a sodium chloride/water solution at a concentration of 5-35% (w/w), or 10-30% (w/w), or 15-25% (w/w), can be sprayed onto the outer surfaces of the gelled alginate matrices of the washed microcapsules mentioned above to obtain a predetermined weight gain, e.g. a weight gain of about 10-50%, or about 15-45%, or about 20-40%, or about 30%, or to obtain a predetermined surface coverage with the sodium chloride solution, e.g. a coverage of at least 30%, at least 50%, at least 70%, or at least 90%. In an alternative embodiment, the gelled alginate matrices may be treated with sodium chloride by dipping or immersing the probiotic bacteria encapsulated in the gelled alginate microcapsules into a sodium chloride/water solution at a concentration of 5-35% (w/w), or 10-30% (w/w), or 15-25% (w/w). In a preferred embodiment, the sodium chloride/water solution contains sodium chloride ions and is substantially free from ionic species such as magnesium chloride, calcium chloride, potassium chloride, and the like.

The shapes of the microcapsules of the current disclosure can vary, including spherical, oval, and cylindrical shapes.

In some embodiments, the microencapsulated probiotic bacteria have an average particle size of 1-1000 microns (μm), 1-800 microns (μm), preferably 1-600 microns (μm), preferably 1-400 microns (μm), preferably 1-200 microns (μm), preferably 1-100 microns (μm), preferably 1-50 microns (μm), preferably 100-700 microns (μm), preferably 200-600 microns (μm), preferably 500-700 microns (μm), preferably 400-600 microns (μm), or preferably 300-500 microns (μm), in diameter.

The gelled alginate that forms the matrix of each of the microcapsules is preferably food-grade. In one embodiment, the gelled alginate that forms the matrix of each of the microcapsules comprises a low viscosity alginate or alginate salt. In another embodiment, the gelled alginate that forms the matrix of each of the microcapsules comprises a medium viscosity alginate or alginate salt. In still another embodiment, the gelled alginate that forms the matrix of each of the microcapsules comprises a high viscosity alginate or alginate salt. The gelled alginate forming the matrix of each of the microcapsules can be ammonia alginate, sodium, potassium, magnesium or calcium alginate.

In some embodiments, the gelled alginate that forms the matrix of each of the microcapsules has a weight average molecular weight of 10,000-600,000 Da, or preferably 25,000-500,000 Da, or preferably 40,000-400,000 Da, or preferably 55,000-300,000 Da, or preferably 70,000-200,000 Da, or preferably 85,000-100,000 Da. In other embodiments, the gelled alginate that forms the matrix of each of the microcapsules has a weight average molecular weight of at least 20,000 Da, at least 50,000 Da, preferably at least 100,000 Da, more preferably at least 250,000 Da, more preferably at least 350,000 Da, or more preferably at least 400,000 Da, or more preferably at least 500,000 Da.

In some embodiments, the thickness of the matrix of the gelled alginate is at least 50 μm, preferably at least 150 μm, more preferably at least 250 μm, more preferably at least 350 μm, more preferably at least 500 μm, more preferably at least 750 μm, more preferably at least 900 μm, or more preferably at least 950 μm. The thickness of the matrix of the gelled alginate is defined as the distance from an interface between the gelled alginate matrix of each microcapsule and the probiotic bacteria, which may be a single probiotic bacterium or a colony or clump of probiotic bacteria, to an outer surface of the gelled alginate matrix. Therefore in such embodiments, the probiotic bacteria are located within the interior of the matrix, whereby the gelled alginate matrix provides a barrier that separates the probiotic bacteria from the surrounding environment with a thickness that is at least 50 μm, preferably at least 150 μm, more preferably at least 250 μm, more preferably at least 350 μm, more preferably at least 500 μm, more preferably at least 750 μm, more preferably at least 900 μm, or more preferably at least 950 μm.

In some embodiments, the gelled alginate that forms the matrix of each of the microcapsules comprises one or more unmodified, or natural alginates.

Natural alginates may be modified to obtain synthetic alginates with improved biocompatibility and more desirable physiochemical properties, such as alginate polymer stability, pore size, and hydrophobicity/hydrophilicity. In other embodiments, the gelled alginate that forms the matrix of each of the microcapsules comprises one or more modified, or synthetic, alginates, such as those disclosed in U.S. Patent Application US20120308650 A1, incorporated herein by reference in its entirety. One embodiment of the modified alginate comprises one or more covalently modified monomers defined by Formula I,

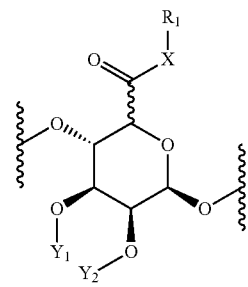

Formula I wherein, X is oxygen, sulfur, or NR; $R_1$ is hydrogen, or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_1$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; $Y_1$ and $Y_2$ independently are hydrogen or —PO(OR)$_2$; or $Y_2$ is absent, and $Y_2$, together with the two oxygen atoms to which $Y_1$ and $Y_2$ are attached form a cyclic structure as shown below,

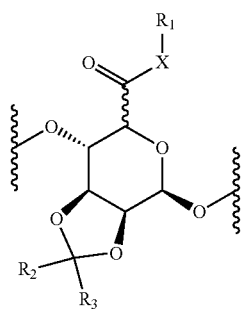

wherein n is an integer between 1 and 4; and $R_2$ and $R_3$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative R groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and R is, independently for each occurrence, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative R groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In other embodiments, the matrix of the gelled alginate comprises a combination of at least one unmodified alginate and at least one modified alginate. In some embodiments, the mass ratio of the modified alginate(s) to the unmodified alginate(s) ranges from 15:1 to 1:15, 10:1 to 1:10, 5:1 to 1:5, 2:1 to 1:2, or 1:1.

Viable bacterial numbers are often reported as CFU, or colony forming units. One colony is formed by a single viable bacterium when the bacteria are plated at a suitable dilution for single colony formation. This is a standard technique known to microbiologists. In some embodiments, the microencapsulated probiotic bacteria comprise at least $1 \times 10^9$ CFU/gram microcapsules of the probiotic bacteria following the encapsulation, such as at least $1 \times 10^{10}$ CFU/gram microcapsules of the probiotic bacteria.

Chitosan is a linear polysaccharide composed of randomly distributed β-(1-4)-linked D-glucosamine (deacetylated unit) and N-acetyl-D-glucosamine (acetylated unit). In some embodiments, the outer surface of the gelled alginate matrix treated with the sodium chloride is also coated with chitosan. The coating with chitosan can be accomplished by immersing the sodium chloride-treated microcapsules containing the probiotic bacteria into a chitosan solution containing about 0.1-0.5% (w/v) of chitosan for an effective period of time, e.g. for 5-60 minutes. Alternatively, a chitosan-containing solution may be sprayed onto the microcapsules to achieve a predetermined weight gain, e.g. a weight gain of about 10-50%, or about 15-45%, or about 20-40%, or about 30%. The chitosan may have a deacetylation degree ranging from 80% to more than 95%. The chitosan may also optionally have a viscosity ranging from 50 mpa to 800 mpa. The chitosan may optionally be trimethylchitosan or quaternised chitosan.

The pH of an aqueous solution to which the probiotic bacteria are exposed can affect the viability of the probiotic bacteria, with lower pH values decreasing the viability of the probiotic bacteria. In one embodiment, the microcapsules protect the probiotic bacteria from being degraded by an acidic aqueous solution.

In some embodiments, the microcapsules protect the probiotic bacteria from being degraded by the acidic aqueous solution, for example, for 0.5-3 hours, preferably for 1-2 hours, and most preferably for 1.5 hours.

In some embodiments, the acidic aqueous solution has a pH of about 0-6, or about 1-5, or about 1-4, or about 1-3.

In some embodiments, the acidic aqueous solution comprises at least one selected from gastric juice, gastric fluid, a simulated gastric juice or fluid, an acidic beverage (e.g. orange juice), dairy products such as milk and yogurt, a food product, and/or an acidic nutritional, pharmaceutical, and/or cosmetic composition. An example of the simulated gastric juice or fluid can comprise 0.08M HCl and 0.2% NaCl with a pH of about 1.55.

In some embodiments, more of the microencapsulated probiotic bacteria are viable and/or metabolically active after a treatment with the acidic aqueous solution than their non-microencapsulated counterparts treated with the acidic aqueous solution. The duration of the treatment is at least about half an hour, preferably at least about 1 hour, preferably at least about 1.5 hours, or preferably at least about 2 hours.

Any suitable assay and/or any suitable biomarker may be used or examined to measure or correlate with the metabolic activity of the probiotic bacteria. In one embodiment, the metabolic activity of the probiotic bacteria can be measured by the AlamarBlue® assay. "AlamarBlue" is a registered trademark name by TREK Diagnostic Systems for an assay that is provided, e.g. by Invitrogen or Promega. The AlamarBlue assay uses the natural reducing power of living bacteria to convert resazurin, a cell permeable compound that is blue in color and virtually non-fluorescent. Upon entering metabolically active bacteria, resazurin, the non-fluorescent indicator dye, is reduced to bright red-fluorescent resorufin. The amount of fluorescence produced is proportional to the number of living bacteria. The fluorescence may be detected with any plate reader or fluorescence spectrophotometer using 560 nm (for excitation)/590 nm (for emission) filter settings. Alternatively, the absorbance of AlamarBlue® can be read on a UV-Vis spectrophotometer at 570 nm.

In other embodiments, the microencapsulated probiotic bacteria have the microcapsules comprising the gelled alginate matrices whose outer surfaces have the coating consisting essentially of the olive oil, and at least 50%, preferably at least 60%, more preferably at least 70%, more preferably at least 80%, or more preferably at least 90%, of the microencapsulated probiotic bacteria survive a treatment with the acidic aqueous solution having a pH of about 1-3 for at least about half an hour, preferably at least about 1 hour, preferably at least about 1.5 hours, or preferably at least about 2 hours.

The treatment with the acidic aqueous solution may be an incubation of the microencapsulated probiotic bacteria in the acidic aqueous solution, and it is a preferred embodiment wherein the treatment is performed under physiological conditions, e.g. a treatment with gastric juice, gastric fluid or simulated gastric juice or fluid. Furthermore, it is preferred that the microencapsulated cells are further protected from intestinal fluids, such as simulated intestinal fluid, or duodenal juice. An example of the simulated intestinal fluid comprises 0.05 M $KH_2PO_4$ and 0.3-0.6% (w/w) bile salts with a pH of 7.43.

With the microcapsules providing sufficient protection for the microencapsulated probiotic bacteria from treatment with acidic aqueous solutions, the microencapsulated probiotic bacteria, after consumption by a human or animal, are now enabled to survive the passage, for example, through the stomach, where the microcapsules are relatively insoluble and impermeable at the pH of the stomach (typically with a pH of about 2 and a retention time of 120 minutes), and into the lower gastrointestinal tract, i.e. either small intestine, or colon, or both, where the microcapsules are more soluble or disintegrable or permeable at the pH of the small intestine and colon (typically with a pH of about 6 and a retention time of 360 minutes) to release the probiotic bacteria conferring health benefits at a higher rate than their non-microencapsulated counterparts.

In some embodiments, the microencapsulated probiotic bacteria are formulated as a supplement for a food or beverage product. Non-limiting examples of the food or beverage product include yogurt, ice cream, cheese, chocolate, nutritional bars, cereal, milk, infant formulation, vegetable juices, and fruit juices. Dairy products, e.g. yogurt, by having such nutrients as amines, metal ions, cofactors, proteins, fat contents, sugars, etc, will provide a further protection for the microencapsulated live probiotic bacterial cells from gastric fluids and other unfavorable gastrointestinal environments.

In one embodiment, if used as a supplement for food such as yogurt, the microencapsulated probiotic bacteria or a composition containing the microencapsulated probiotic bacteria can be stored in a separate compartment of a food package that contains the food. For example, the separate compartment may be bendable to allow its content, i.e. the microencapsulated probiotic bacteria or the composition containing the same, to empty into the other compartment of the food packaging which is filled, for example, with yoghurt. Using such a separate compartment allows addition of, for example, the microencapsulated probiotic bacteria to food only before its consumption.

In another embodiment, the microcapsules comprising the probiotic bacteria are added to a food or beverage product and the food or beverage product is packaged for eventual consumption by an individual. When the food or beverage product is entirely or mostly an aqueous solution in nature, the addition of one or more food-grade, or FDA-approved, surfactants to the product will facilitate the dispersion of the microencapsulated probiotic bacteria with the outer surfaces of the gelled alginate matrices coated with olive oil and/or canola oil. Non-limiting examples of the surfactants include lecithin, monoglycerides, and sorbitan esters and their ethoxylates and sucrose esters, e.g. esters of monostearate or mono-oleate with organic carboxylic acids, e.g., citric acid.

The amount of the microcapsules incorporated into a food or beverage product varies, depending on the loading of viable probiotic bacteria in the microcapsules. In some embodiments, the food or beverage product comprises between 0.05 grams and 10.0 grams of microcapsules per unit measure of product (e.g., fluid ounce or gram of product), or between 0.1 grams and 8 grams of microcapsules per unit measure of product, or between 0.1 grams and 5 grams of microcapsules per unit measure of product, or between 0.1 grams and 3 grams of microcapsules per unit product, or between 0.1 and 1 gram of microcapsules per unit product. A preferred amount of viable probiotic bacteria in a food or beverage product comprises at least $1 \times 10^{10}$ CFU per serving of product. It will be within the abilities of one skilled in the art to determine an appropriate amount of the microcapsules to include in a specific product to provide at least $1 \times 10^9$ CFU, preferably at least $5 \times 10^{10}$ CFU, per serving of product. In some embodiments, the food or beverage product is heated to pasteurize before the addition of the microcapsules comprising the probiotic bacteria. Alternatively, the microcapsules comprising the probiotic bacteria may be introduced to the food product in a separate packing that allows the user to mix the microcapsules with the food product just prior to consumption. To maintain the viability of the probiotic bacteria in the microcapsules with a food or beverage product, refrigeration is preferred, with the temperatures range from, for example, from about 32° F. to 50° F. (0° C. to 10° C.), or from about 35° F. to 43° F. (2° C. to 6° C.).

In addition, it is contemplated that the microencapsulated probiotic bacteria will not affect desired physical properties of the food or beverage product. For example, it is contemplated that the microcapsules will not affect acceptable mouthfeel, or physical and chemical interactions with the mouth, or the taste of the finished product. In some embodiments, the average particle size of the microencapsulated probiotic bacteria should be small enough not to increase the viscosity of the product or to provide a noticeable change in the taste of the product.

In some embodiments, the microencapsulated probiotic bacteria may be formulated as or included in a pharmaceutical or nutraceutical composition. In the composition, the microencapsulated probiotic bacteria may further comprise a pharmaceutically acceptable excipient and/or a suitable carrier, and an appropriate amount of the microcapsules may be contained in a pill, a (macro-)capsule (with an enteric coating), a medicinal syrup, or the like, for convenient oral administration. The pharmaceutical or nutraceutical composition can be administered to a subject, usually a mammal such as human or a domestic animal or a farm animal such as cats, dogs, sheep, cows, pigs, poultry or fish, to name only few illustrative examples.

In other embodiments, the microencapsulated probiotic bacterial may be formulated as a cosmetic composition or an additive thereof. Examples of cosmetic compositions in which the microencapsulated probiotic bacteria can be included are topical compositions such as soaps (both liquid or solid), lotions, makeup, creams, shower gels, bathing salts, or hair wash. Illustrative examples of such compositions include probiotic bacterial strains such as *Lactobacillus, Bifidobacterium* or *Bacillus coagulans*, for example the strain GanedenBC$^{30}$® (*Bacillus coagulans* GBI-30, 6086 of Ganeden Biotec, Cleveland, Ohio, USA). Such cosmetic composition can, for example, be used to improve skin hydration, elasticity, under eye puffiness, or to reduce fine lines and wrinkles in humans.

In another embodiment, the microcapsules protect the probiotic bacteria from being degraded by an aqueous solution comprising bile salts at a concentration of about 0.1-1% of the total weight of the aqueous solution.

In some embodiments, the concentration of the bile salts in the aqueous solution is about 0.1-1%, or about 0.2-0.9%, or about 0.3-0.8%, or about 0.4-0.7%, or about 0.5-0.6%, of the total weight of the aqueous solution.

In some embodiments, the aqueous solution containing the bile salts comprises at least one selected from the group consisting of intestinal juice and a simulated intestinal juice or fluid. In some embodiments, the aqueous solution containing the bile salts has a pH of about 6-11, or about 7-10, or about 8-9.

In some embodiments, more of the microencapsulated probiotic bacteria are viable and/or metabolically active after a treatment with the aqueous solution comprising the bile salts at a concentration of about 0.1-1%, or about 0.2-0.9%, or about 0.3-0.8%, or about 0.4-0.7%, or about 0.5-0.6%, of the total weight of the aqueous solution than their non-microencapsulated counterparts treated with the same bile salt containing aqueous solution. The duration of the treatment is at least about 15 minutes, preferably at least about 30 minutes, more preferably at least about 1 hour, more preferably at least 1.5 hours, or more preferably at least about 2 hours.

In some embodiments, the microencapsulated probiotic bacteria have the microcapsules comprising the gelled alginate matrices whose outer surfaces are treated with the sodium chloride, and at least 50%, preferably at least 60%, more preferably at least 70%, more preferably at least 80%, more preferably at least 90%, or more preferably at least 98%, of the microencapsulated probiotic bacteria survive a treatment with the aqueous solution comprising the bile salts at a concentration of about 0.1-0.6%, or about 0.2-0.5%, or about 0.3-0.4%, of the total weight of the aqueous solution for at least about 15 minutes, preferably at least about 30 minutes, more preferably at least about 1 hour, more preferably at least about 1.5 hours, or more preferably at least about 2 hours.

In other embodiments, the microencapsulated probiotic bacteria have the microcapsules comprising the gelled alginate matrices whose outer surfaces have the coating consisting essentially of the olive oil, and at least about 50%, preferably at least about 60%, more preferably at least about 70%, more preferably at least about 80%, or more preferably at least about 90%, of the microencapsulated probiotic bacteria survive a treatment with the aqueous solution comprising the bile salts at a concentration of about 0.1-1%, or about 0.2-0.9%, or about 0.3-0.8%, or about 0.4-0.7%, or about 0.5-0.6%, of the total weight of the aqueous solution for at least about 15 minutes, preferably at least about 30 minutes, more preferably at least about 1 hour, more preferably at least 1.5 hours, or more preferably at least about 2 hours.

In still another embodiment, the microcapsules protect the probiotic bacteria from being degraded at a temperature of at least 65° C. for at least 15 minutes.

In some embodiments, more of the microencapsulated probiotic bacteria are viable and/or metabolically active after being exposed to a temperature of at least 45° C., at least 55° C., at least 65° C., at least 70° C., at least 75° C., at least 80° C., or at least 85° C., for at least about 1 minute, at least about 5 minutes, at least about 10 minutes, at least about 15 minutes, at least about 20 minutes, or at least about 30 minutes, than their non-microencapsulated counterparts treated under the same conditions.

In other embodiments, the decrease of viable probiotic bacteria upon subjection to the elevated temperatures indicated above ranges from 0 to $1.0 \times 10^4$ CFU/gram microcapsules, or from 0 to $5.0 \times 10^3$ CFU/gram microcapsules, or from 0 to $1.0 \times 10^3$ CFU/gram microcapsules, or from 0 to $5.0 \times 10^3$ CFU/gram microcapsules, or from 0 to $1.0 \times 10^2$ CFU/gram microcapsules, or from 0 to 50 CFU/gram microcapsules, or 0 to 10 CFU/gram microcapsules. Typically, the higher the temperature, the shorter the time duration is for which the probiotic bacteria will be successfully thermally protected. The disclosed thermal protection of the microencapsulated probiotic bacteria by the microcapsules is advantageous, for example, when the microencapsulated probiotic bacteria are part of a food, e.g. baking goods and products, yogurt, and hot drinks, a cosmetic or pharmaceutical product subjected to thermal processing during preparation and/or destruction of undesirable microbes, since sufficient numbers of viable bacteria may be necessary to obtain the beneficial effects of the probiotic bacteria.

In still other embodiments, the microencapsulated probiotic bacteria have the microcapsules comprising the gelled alginate matrices whose outer surfaces are treated with the sodium chloride, and at least about 50%, preferably at least about 60%, more preferably at least about 70%, more preferably at least about 80%, or more preferably at least about 90%, of the microencapsulated probiotic bacteria survive at a temperature of at least 45° C., at least 55° C., at least 65° C., at least 70° C., at least 75° C., at least 80° C., or at least 85° C., for at least 1 minute, at least 5 minutes, at least 10 minutes, at least 15 minutes, at least 30 minutes, at least 45 minutes, or at least 1 hour.

The microencapsulated probiotic bacteria, or a food or beverage product or a pharmaceutical or nutraceutical composition comprising the microencapsulated probiotic bacteria can be administered orally, without limitation, to treat or prevent gastrointestinal tract related diseases or cancer, such as diarrhea, diarrhea caused by antibiotic, arthritis, obesity, irritable bowel syndrome, heartburn, chronic fatigue syndrome and other forms of suffering from an unbalanced bacterial population in the intestine, to repopulate the gut after antibiotic therapy, offset lactose intolerance, support the immune system and reduce cholesterol, enhance the bio-availability of calcium, zinc, iron, manganese, copper and phosphorus and synthesis of vitamins, inhibit pathogenic bacteria and colon cancer growth. Non-limiting examples of a subject receiving and benefiting from such an oral administration include a mammal such as human or a domestic animal or a farm animal such as cats, dogs, sheep, cows, pigs, poultry or fish. In a preferred embodiment, the microencapsulated probiotic bacteria are carried in fermented milk, such as yogurt, since the microencapsulated probiotic bacteria survive gastric conditions significantly better when stored in yogurt as opposed to storage in many other media. Several factors affect the protective effect of yogurt on probiotic bacteria. These include the strains of the probiotic bacteria, pH, hydrogen peroxide, storage atmosphere, concentration of metabolites such as lactic acid and acetic acids, dissolved oxygen, and buffers such as whey proteins. An initial bacteria load of $10^7$ CFU/g of yogurt is recommended by the National Yogurt Association for yogurt to be called a probiotic. These high numbers have been suggested to compensate for the possible loss in the numbers of the probiotic bacteria during passage through the stomach and intestine. Preferably, a higher bacteria load of $10^{10}$ CFU/g of yogurt is used to ensure delivery of a greater number of live probiotic bacteria to the target sites, e.g. small intestines and colon.

A second aspect of the disclosure relates to microencapsulated probiotic bacteria comprising probiotic bacteria encapsulated in microcapsules. The probiotic bacteria comprise live *Lactobacillus plantarum* cells. Each of the microcapsules comprises a matrix of a gelled alginate. The matrix wholly envelops the probiotic bacteria within the matrix. An outer surface of the matrix has a coating consisting essentially of olive oil. The microencapsulated probiotic bacteria have an average particle size of less than 1000 microns (μm) in diameter. The microcapsules protect the probiotic bacteria from being degraded at a temperature of about −30-10° C. for at least 7 days.

In some embodiments, the microencapsulated probiotic bacteria of this aspect have the same characteristics as the microencapsulated probiotic bacteria with the microcapsules comprising the gelled alginate matrices whose outer surfaces have the coating consisting essentially of the olive oil described in the first aspect.

The structure of the microencapsulated probiotic bacteria of this aspect of the disclosure ensures their high stability, or viability, during storage at a low temperature, typically below an ambient temperature. In some embodiments, at least about 50%, preferably at least about 60%, more preferably at least about 70%, more preferably at least about 80%, or more preferably at least about 90%, of the microencapsulated probiotic bacteria remain viable at a temperature of about −30-10° C., about −20-4° C., or about −10-0° C., for at least about 7 days, at least about 10 days, at least about 14 days, at least about 20 days, or at least about 30 days.

In other embodiments, more of the microencapsulated probiotic bacteria are viable and/or metabolically active after being exposed to a temperature of about −30-10° C., about −20-4° C., or about −10-0° C., for at least about 7 days, at least about 10 days, at least about 14 days, at least about 20 days, or at least about 30 days than their non-microencapsulated counterparts treated under the same conditions.

A third aspect of the disclosure relates to microencapsulated probiotic bacteria comprising probiotic bacteria encapsulated in microcapsules. The probiotic bacteria comprise live *Lactobacillus plantarum* cells. Each of the microcapsules comprises a matrix of a gelled alginate. The matrix wholly envelops the probiotic bacteria within the matrix. An outer surface of the matrix has a coating consisting essentially of one selected from the group consisting of olive oil, canola oil, a combination of olive oil and canola oil, and chitosan, or an outer surface of the matrix is treated with sodium chloride. The microencapsulated probiotic bacteria have an average particle size of less than 1000 microns (μm) in diameter, and the microencapsulated probiotic bacteria display an increased anti-bacterial activity as compared to the probiotic bacteria not encapsulated in microcapsules.

In some embodiments, the microencapsulated probiotic bacteria of this aspect have the same characteristics as the microencapsulated probiotic bacteria with the microcapsules comprising the gelled alginate matrices whose outer surfaces have the coating consisting essentially of at least one vegetable oil selected from the group consisting of olive oil and canola oil, or whose outer surfaces are treated with the sodium chloride, as described in the first aspect.

In some embodiments, the microcapsules comprise the gelled alginate matrices whose outer surfaces have a coating consisting essentially of chitosan. The chitosan is at least 90% pure, preferably at least 95% pure, or more preferably at least 98% pure. Trace amounts of impurities from the chitosan preparation, such as beta-glucan of no greater than 5% (w/w), proteins of no greater than 1% (w/w), and/or bacterial endotoxins of no greater than 10 EU/g, and/or chemicals used in the coating procedure, such as the solvent used to dissolve the chitosan, e.g. acetic acid, will not affect the anti-bacterial activity of the encapsulated probiotic bacteria. The coating with chitosan can be accomplished by immersing the washed, uncoated microcapsules prepared, for example, by an extrusion method, as described in the first aspect, and containing the probiotic bacteria into a chitosan solution containing about 0.1-0.5% (w/v) of chitosan for an effective period of time, e.g. for 5-60 minutes. Alternatively, a chitosan-containing solution may be sprayed onto the microcapsules to achieve a predetermined weight gain, e.g. a weight gain of about 10-50%, or about 15-45%, or about 20-40%, or about 30%. The chitosan may have a deacetylation degree ranging from 80% to more than 95%. The chitosan may also optionally have a viscosity ranging from 50 mpa to 800 mpa. The chitosan may optionally be trimethylchitosan or quaternised chitosan.

In other embodiments, the microcapsules comprise the gelled alginate matrices whose outer surfaces are treated with sodium chloride and also coated with chitosan. Using the same procedure described in the first aspect, the coating with chitosan can be accomplished by immersing the sodium chloride-treated microcapsules containing the probiotic bacteria into a chitosan solution containing about 0.1-0.5% (w/v) of chitosan for an effective period of time, e.g. for 5-60 minutes. Alternatively, a chitosan-containing solution may be sprayed onto the microcapsules to achieve a predetermined weight gain, e.g. a weight gain of about 10-50%, or about 15-45%, or about 20-40%, or about 30%. The chitosan may have a deacetylation degree ranging from 80% to more than 95%. The chitosan may also optionally have a viscosity ranging from 50 mpa to 800 mpa. The chitosan may optionally be trimethylchitosan or quaternised chitosan.

In some embodiments, the anti-bacterial activity of the microencapsulated probiotic bacteria and their non-microencapsulated counterparts can be measured and compared by the well diffusion assay well known in the art. In other embodiments, the anti-bacterial activity of the microencapsulated probiotic bacteria and their non-microencapsulated counterparts can be measured and compared by measuring the activity and/or amounts of bacterial inhibiting enzymes, metabolites, and/or substances (in the form of mRNA and/or protein, for example), non-limiting examples of which include short chain fatty acids such as acetic acid, lactic acid or propionic acid, hydrogen peroxide, and bacteriocins.

The microencapsulated probiotic bacteria may display an increased anti-bacteria activity against at least one of Gram negative and Gram positive bacteria, including, but not limited to, *E. coli, P. aeruginosa, E. aerogenes*, and *S. pyogenes*.

In some embodiments, there is an increase of at least 5%, at least 10%, at least 20%, at least 30%, at least 40%, at least 60%, at least 80%, at least 100%, or at least 200% in the anti-bacterial activity of the microencapsulated probiotic bacteria as compared to their non-microencapsulated counterparts.

In some embodiments, the increased anti-bacterial activity is displayed by the intact probiotic bacterial cells wholly enveloped by the matrices of the microcapsules. The intact probiotic bacterial cells may be live probiotic bacterial cells, or inactivated or killed probiotic bacterial cells that contain active anti-bacterial enzymes, substances, and/or metabolites.

In other embodiments, the increased anti-bacterial activity is displayed by the lysates obtained from the microencapsulated probiotic bacteria. The lysates refer to samples of the probiotic bacteria which have been subject to lysis. Lysis may occur by chemical or physical disruption, for example by addition of an osmotic agent, and/or an enzyme (e.g. lysozyme), and/or a detergent (e.g. Triton X-100, NP-40, and SDS) to the bacteria, or by the application of physical pressure, for example through sonic disruption. Lysed cells may allow the release of many substances, including soluble anti-bacterial enzymes and metabolites, from inside the bacterial cell membrane. The bacteria may be washed prior to lysis.

A lysate may thus contain one or more soluble anti-bacterial enzymes, substances, and/or metabolites of the probiotic bacteria. The lysate may be filtered and/or sterilized after lysis to remove any whole bacteria remaining. The lysate may be a mixture comprising the cellular contents of the probiotic bacteria. For example, one or more of fragments of cell wall or cell membrane, proteins, nucleic acids, carbohydrates, and organelles (disrupted or intact). The lysate may be suspended, for example in aqueous medium.

The lysate may comprise a cell free supernatant, i.e. the supernatant of a probiotic bacterial culture from which the bacterial cells have been removed. The probiotic bacterial cells may be removed by centrifugation, and the supernatant may be filtered. A cell free supernatant may contain one or more secreted anti-bacterial enzymes, substances, and/or metabolites.

In some embodiments, the increased anti-bacterial activity is displayed by the microencapsulated probiotic bacteria that have been treated with an acidic aqueous solution as described in this disclosure.

In some embodiments, the increased anti-bacterial activity is displayed by the microencapsulated probiotic bacteria that have been treated with an aqueous solution comprising bile salts at a concentration of 0.1-1% as described in this disclosure.

In some embodiments, the increased anti-bacterial activity is displayed by the microencapsulated probiotic bacteria that have been sequentially treated with an acidic solution, e.g. a simulated gastric fluid, followed by an aqueous solution comprising bile salts at a concentration of 0.1-1%, e.g. a simulated intestinal fluid.

In some embodiments, the increased anti-bacterial activity is displayed by the microencapsulated probiotic bacteria that have been exposed to elevated temperatures, e.g. at least 65° C. for at least 15 minutes, as described in this disclosure.

In some embodiments, the increased anti-bacterial activity is displayed by the microencapsulated probiotic bacteria that have been stored at a low temperature for a prolonged period of time, e.g. at −30-10° C. for at least 7 days, as described in this disclosure.

Having generally described this invention, a further understanding can be obtained by reference to certain specific examples which are provided herein for purposes of illustration only and are not intended to be limiting unless otherwise specified.

Example 1

Comparison of the Growth Rates of the Probiotic Bacterial Strains *Lactobacillus plantarum, Lactobacillus casei, Lactobacillus acidophilus*, and *Bifidobacterium bifidum* Under Low pH and High Bile Salt Conditions Four strains of probiotic bacteria *Lactobacillus plantarum* DSM 20174, *Lactobacillus casei* DSM 20011, *Lactobacillus acidophilus* DSM 20079, and *Bifidobacterium* bifidum DSM 20456 were obtained from Deutsche Sammlung von Mikroorganismen DSM and Zellkultturen. GmbH. Germany.

The growth rates of the four probiotic bacterial strains were compared by measuring OD620 nm with a spectrophotometer. *L. plantarum* showed the greatest growth rate after 7 hours of incubation, followed by *L. casei* after 24 hours of incubation, whereas *L. acidophilus* and *B. bifidum* displayed lower growth rates. All four strains grew in numbers up to 48 hours that began to decline afterwards.

The viability or stability of the probiotic bacterial strains at low pH conditions was studied by adjusting the hydrogen ion concentration in liquid MRS media and inoculating the bacteria into the media followed by incubation under optimal conditions. The growth of the bacteria was monitored hourly for 24 hours by measuring OD620 nm with a spectrophotometer. There was a decrease in the ability of all the probiotic bacterial strains to withstand the conditions of pH 1 and pH 2 after 24 hours of incubation, with the growth rates ranging from 2.41% to 14.40% at pH 1, and ranging from 7.26% to 47.04% at pH 2, while all the bacterial strains were able to grow better at pH 3, with the growth rates ranging from 27.78% to 68.90%. Among the probiotic bacterial strains, *L. acidophilus* and *L. plantarum* showed the highest ability to withstand the acidic condition of pH 3.

A study on the stability of the probiotic bacterial strains at high concentrations of bile salts was done by adding two different concentrations of bile salts (0.3% and 0.5%) to the liquid MRS media and inoculating the bacteria into the media followed by incubation under optimal conditions. The growth of the bacteria was likewise monitored hourly for 24 hours by measuring OD620 nm with a spectrophotometer. All the probiotic bacterial strains were able to withstand the bile salts at the concentration of 0.3%, with the growth rates ranging from 7.25% to 93.20%. However, all the strains showed a lower ability to withstand the bile salts at the higher concentration of 0.5%, with *L. plantarum* being the best able and *B. bifidum* being the least able to withstand the higher concentration of the bile salts.

Example 2

Comparison of the Antibacterial Activity of the Probiotic Bacterial Strains *Lactobacillus plantarum, Lactobacillus casei, Lactobacillus acidophilus*, and *Bifidobacterium bifidum*

The ability of the probiotic bacterial strains *Lactobacillus plantarum*, *Lactobacillus casei*, *Lactobacillus acidophilus*, and *Bifidobacterium bifidum* to inhibit the growth of pathogenic bacteria was studied by using the well diffusion assay with the probiotic bacterial lysates cleared of intact probiotic bacterial cells and/or insoluble cell debris by centrifugation. *L. plantarum* showed the strongest antibacterial activity against all the Gram negative and Gram positive pathogenic bacteria tested with the exception of *S. pneumonia*, followed by *L. casei* that showed an antibacterial activity against *E. coli*, *P. aeruginosa*, *E. aerogenes* and *S. pyogenes*. *L. acidophilus* showed a moderate antibacterial activity against *P. aeruginosa* and *E. aerogenes* and a strong antibacterial activity against *S. pyogenes*. *B. bifidum* showed a strong antibacterial activity against the Gram positive bacterial strains *S. pyogenes* and *S. pneumonia*. In general, the antibacterial activity of the probiotic bacterial strains varies, depending on the genus and the species.

Example 3

Microencapsulation of *L. plantarum* and Comparison of the Viability Between the Microencapsulated *L. plantarum* Cells and their Non-Microencapsulated Counterparts Under Conditions of Low pH, High Bile Salt Concentrations, an Elevated Temperature, and Prolonged Storage at a Low Temperature Using extrusion technology, *L. plantarum* cells were microencapsulated, with the outer surfaces of the gelled alginate matrices of the microcapsules treated with sodium chloride, or the outer surfaces of the gelled alginate matrices of the microcapsules coated with olive oil, canola oil, or chitosan. The resulting microcapsules varied in texture, shape and hardness. The microcapsules comprising the gelled alginate matrices whose outer surfaces were treated with the sodium chloride were semi-solid and oval or round-shaped with regular declines. The microcapsules comprising the gelled alginate matrices whose outer surfaces were coated with the olive oil or the canola oil were spherical and soft, and had rough surfaces with round declines in the center. The microcapsules comprising the gelled alginate matrices whose outer surfaces were coated with the chitosan were spherical in shape with indentation on the surfaces.

The stability of the microencapsulated *L. plantarum* cells and their non-microencapsulated counterparts under low pH conditions simulating those of the stomach was examined and compared, by incubating the microencapsulated *L. plantarum* cells and their non-microencapsulated counterparts in liquid MRS media with a low pH of 2 or 3. At pH 2, the microencapsulated *L. plantarum* cells, particularly those with the microcapsules comprising the gelled alginate matrices whose outer surfaces were coated with the olive oil, displayed a significant increase in stability as compared to their non-microencapsulated counterparts. At pH 3, the microencapsulated *L. plantarum* cells were also more stable than their non-microencapsulated counterparts. Among the microencapsulated *L. plantarum* cells at pH 3, those with the microcapsules comprising the gelled alginate matrices whose outer surfaces were treated with the sodium chloride were the most stable, followed by, in descending order of stability, those with the microcapsules comprising the gelled alginate matrices whose outer surfaces were coated with the olive oil, those with the microcapsules comprising the gelled alginate matrices whose outer surfaces were coated with the chitosan, and those with the microcapsules comprising the gelled alginate matrices whose outer surfaces were coated with the canola oil. Overall, the microcapsules comprising the gelled alginate matrices whose outer surfaces were coated with the olive oil conferred the best stability at a low pH of between 2 and 3.

The stability of the microencapsulated *L. plantarum* cells and their non-microencapsulated counterparts exposed to a high concentration of bile salts was examined and compared. When exposed to an aqueous solution containing 0.3% (w/w) bile salts, the microencapsulated *L. plantarum* cells with any one type of the microcapsules were more stable than their non-microencapsulated counterparts. In particular, the *L. plantarum* cells with the microcapsules comprising the gelled alginate matrices whose outer surfaces were treated with the sodium chloride displayed a high stability of up to 98.8%. When exposed to an aqueous solution containing 0.5% (w/w) bile salts, the microencapsulated *L. plantarum* cells, regardless of the type of the microcapsules, were less stable than they were when exposed to the aqueous solution containing 0.3% (w/w) bile salts, with those having the microcapsules comprising the gelled alginate matrices whose outer surfaces were treated with the sodium chloride being affected the most. When exposed to the aqueous solution containing 0.5% (w/w) bile salts, the microencapsulated *L. plantarum* cells with the microcapsules comprising the gelled alginate matrices whose outer surfaces were coated with the olive oil or the chitosan were more stable than the microencapsulated *L. plantarum* cells with the other two types of the microcapsules.

Due to the importance of heat treatment, e.g. during the pasteurization of foods, the ability of the microencapsulated probiotic bacteria to withstand an elevated temperature of 65° C. for 15 and 30 minutes was studied. The elevated temperature had an adverse effect on the non-microencapsulated probiotic bacterial cells, since they were completely lost following the exposure to 65° C. for 15 minutes. By contrast, the microencapsulated probiotic bacteria were able to remain stable at 65° C. for up to 30 minutes. Specifically, the microencapsulated probiotic bacteria with the microcapsules comprising the gelled alginate matrices whose outer surfaces were coated with the chitosan or treated with the sodium chloride were stable at 65° C. for 30 minutes, while the microencapsulated probiotic bacteria with the microcapsules comprising the gelled alginate matrices whose outer surfaces were coated with the olive oil or the canola oil were stable at 65° C. for 15 minutes.

Storing dairy products containing probiotic bacteria at low temperatures has an important role in maintaining the viability of the probiotic bacteria. Both the microencapsulated probiotic bacteria and their non-microencapsulated counterparts were stored at 4° C. for 17 days, with their viability/stability measured every 4 days. The microencapsulated *L. plantarum* cells with the microcapsules comprising the gelled alginate matrices whose outer surfaces were coated with the chitosan had the highest stability during two weeks (14 days) of storage, followed by the microencapsulated *L. plantarum* cells with the microcapsules comprising the gelled alginate matrices whose outer surfaces were coated with the olive oil. By contrast, the microencapsulated *L. plantarum* cells with the microcapsules comprising the gelled alginate matrices whose outer surfaces were treated with the sodium chloride or coated with the canola oil did not show any difference from their non-microencapsulated counterparts.

Example 4

Comparison of the Antibacterial Activity Between the Microencapsulated *L. plantarum* Cells and their Non-Microencapsulated Counterparts The microencapsulated *L. plantarum* cells with any one of the four types of the microcapsules displayed an increased antibacterial activity against an array of Gram-negative and Gram positive pathogenic bacteria.

Example 5

Comparison of the Stability in Yogurt Between the Microencapsulated *L. plantarum* Cells and their Non-Microencapsulated Counterparts The microencapsulated *L. plantarum* bacteria with the microcapsules comprising the gelled alginate matrices whose outer surfaces were coated with the chitosan and their non-microencapsulated counterparts were added separately to yogurt made from fresh cow milk plus *Streptococcus thermophilus* and *Lactobacillus bulgaricus*. The microencapsulated *L. plantarum* cells were more stable and viable than their non-microencapsulated counterparts in the yogurt. There were no differences in the sensory properties, e.g. taste, color, aroma and texture, in the rheological properties, e.g. viscosity, or in the chemical characteristics, e.g. pH, between the yogurt supplemented with the microencapsulated *L. plantarum* bacteria and that supplemented with their non-microencapsulated counterparts.

The invention claimed is:

1. A probiotic dairy food, comprising:
a yogurt, and
*Lactobacillus plantarum* bacteria encapsulated in extruded microcapsules, wherein the *Lactobacillus plantarum* bacteria are live and the extruded microcapsules are mixed with the yogurt,
wherein the extruded microcapsules comprise a matrix of a gelled alginate within which the *Lactobacillus plantarum* bacteria are encapsulated,
wherein outer surfaces of the extruded microcapsules are coated with a coating consisting essentially of olive oil
wherein the olive oil coating the extruded microcapsules is present in an amount corresponding to a weight gain of about 10% to 50% relative to a weight of the extruded microcapsules prior to application of the olive oil, and
wherein the extruded microcapsules have an average particle size of less than 1000 microns (μm) in diameter, and
wherein a minimum of $10^7$ *Lactobacillus plantarum* bacteria are alive per gram of the yogurt.

2. The probiotic dairy food of claim 1, wherein the gelled alginate is an unmodified alginate, a modified alginate, or a combination thereof.

3. The probiotic dairy food of claim 1,
wherein at least 80% of the encapsulated *Lactobacillus plantarum* bacteria survive a treatment with an acidic aqueous solution having a pH of about 1-3 for at least 1.5 hours.

4. The probiotic dairy food of claim 1, wherein at least 80% of the encapsulated *Lactobacillus plantarum* bacteria survive a treatment with an aqueous solution comprising bile salts at a concentration of about 0.4-0.7% of the total weight of the aqueous solution for at least 2 hours.

* * * * *